United States Patent [19]

Marhold et al.

[11] 4,155,940
[45] May 22, 1979

[54] m-BROMO-BENZOTRIFLUORIDES

[75] Inventors: Albrecht Marhold, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 876,821

[22] Filed: Feb. 10, 1978

[30] Foreign Application Priority Data

Feb. 25, 1977 [DE] Fed. Rep. of Germany ....... 2708190

[51] Int. Cl.² .............................................. C07C 25/14
[52] U.S. Cl. ............................. 260/651 F; 260/650 F
[58] Field of Search ..................................... 260/651 F

[56] References Cited

U.S. PATENT DOCUMENTS

| | | | |
|---|---|---|---|
| 3,258,500 | 6/1966 | Swamer et al. | 260/651 F |
| 3,742,074 | 6/1973 | Hermann et al. | 260/651 F |
| 3,859,372 | 1/1975 | Robote | 260/651 F |
| 4,045,502 | 8/1977 | Bhutani et al. | 260/651 F |
| 4,080,392 | 3/1978 | Ryf | 260/651 F |

OTHER PUBLICATIONS

Paulath et al., Aromatic Fluorine Compounds, Reinhold Pub. Corp., N.Y. (1962), p. 112.

*Primary Examiner*—C. Davis
*Attorney, Agent, or Firm*—Sprung, Felfe, Horn, Lynch & Kramer

[57] ABSTRACT

A process for preparing an m-bromo-benzotrifluoride by brominating an unsubstituted, halo or alkyl substituted benzotrichloride in the presence of a catalyst and thereafter fluorinating the brominated product at elevated temperature and pressure. Also disclosed are new m-bromo-benzotrifluorides including 4-fluoro-3-bromobenzotrifluoride and 4-methyl-3-bromobenzotrifluoride.

13 Claims, No Drawings

M-BROMO-BENZOTRIFLUORIDES

BACKGROUND OF THE INVENTION

1. FIELD OF THE INVENTION

The invention relates to a process for the preparation of m-bromo-benotrifluorides.

2. DISCUSSION OF THE PRIOR ART

It is known to prepare 3-bromo-4-chloro-benzotrifluoride by brominating 4-chloro-benzotrifluoride, using iron as a catalyst (J. Am. Chem. Soc. 71, 2659 (1949)). The yield of the process is about 55%. A large proportion of the 4-chlorobenzotrifluoride employed is saponified to the corresponding carboxylic acid during the process. The 4-chlorobenzotrifluoride must in turn be prepared by fluorinating 4-chlorobenzotrichloride.

It is also known to carry out the bromination of trifluoromethylbenzenes in the presence of antimony pentachloride as a catalyst (J. Am. Chem. Soc. 72, 1651 (1950)). In this reaction, the yield is only about 30 to 35%.

SUMMARY OF THE INVENTION

A process has been found for the preparation of m-bromo-benzotrifluorides, in which a benzotrichloride of the formula

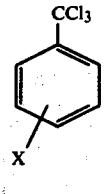

wherein

X denotes hydrogen, halogen or a $C_1$–$C_4$ alkyl radical, is first brominated in the presence of a catalyst, and the product is then reacted with hydrofluoric acid at elevated temperature and under elevated pressure.

The process according to the invention is illustrated with the aid of the following equation for the preparation of 3-bromo-4-chloro-benzotrifluoride:

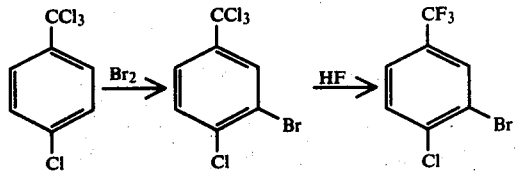

Halogens (X) for the process according to the invention can be fluoride, chloride, bromine or iodine, preferably fluoride or chlorine.

An alkyl radical (X) can be a straight-chain or branched aliphatic hydrocarbon radical with 1 to 4 carbon atoms. In detail, there may be mentioned methyl, ethyl, propyl, isopropyl, butyl and isobutyl, preferably methyl and ethyl.

Friedel-Crafts catalysts may be mentioned as catalysts for the bromination. All the catalysts customary for Friedel-Crafts reactions can be used as the Friedel-Crafts catalysts. Examples which may be mentioned are iron powder, iron sulphide, iron chloride, iron bromide, aluminium bromide and aluminium chloride, preferably iron sulphide and iron.

The amount of catalyst can vary from 0.2 to 1% by weight, preferably 0.3 to 0.5% by weight, relative to the benzotrichloride. The bromination step of the process according to the invention can be carried out in the temperature range from 0° to 100° C., preferably 20° to 70° C., and particularly preferably from 30° to 60° C.

The bromination step can be carried out under normal pressure or under excess pressure. In general, the bromination step is carried out under normal pressure. In order to prevent the bromine from distilling off, it can be advantageous to carry out the process under elevated pressure.

The process according to the invention is preferably carried out without a solvent or diluent. However, it is also possible to carry out the process in solvents or diluents which are inert under the reaction conditions. Examples of these which may be mentioned are: chlorinated hydrocarbons, such as chloroform, carbon tetrachloride and tetrachloroethylene.

In general, the fluorination step of the process according to the invention is carried out in the temperature range of about −10 to 120° C., preferably of 60 to 100° C. A lower temperature is employed when using an additional fluorinating catalyst, for example antimony pentachloride or a Friedel-Crafts catalyst as mentioned above, an elevated temperature is employed when using anhydrous hydrofluoric acid only as the performance of the fluorinating step is possible even without a catalyst.

The fluorination step of the process according to the invention is carried out under elevated pressure. In general, the fluorination step is carried out in the pressure range of 3 to 40 bars, preferably of 6 to 10 bars.

Antimony trifluoride and, in particular, anhydrous hydrofluoric acid, have proved to be suitable fluorinating agents.

The process according to the invention is generally carried out as a "one-pot process", that is to say without isolating the bromination product obtained during the bromination. The bromination product predominantly consists of optionally substituted m-bromo-benzotrichloride, which is a new chemical compound. However, it is, of course, also possible to isolate the bromination product.

The process according to the invention can be carried out as follows:

The benzotrichloride and the catalyst are initially introduced into the reaction vessel, appropriately an autoclave, and the bromine is added dropwise at the chosen reaction temperature. After the bromination has ended, an inert gas, for example nitrogen, is passed through the reaction mixture in order to expel excess bromine.

The reaction mixture is then cooled, the hydrofluoric acid is added and excess pressure is established in the autoclave with the aid of the inert gas. It is warmed up to the reaction temperature of the fluorination stage. The hydrogen chloride gas formed is let down via a regulating valve, with the aid of which the reaction pressure can be adjusted.

After the reaction has ended, the reaction mixture is let down and is worked up in the customary manner by steam distillation or fractional distillation.

Compared with the known processes for the preparation of m-bromo-benzotrifluorides, the process according to the invention has the considerable advantages that it gives a substantially improved yield, that is to say 70–80% of theory instead of the 30–50% achieved hitherto, and that m-bromo-benzotrifluorides which have not yet hitherto been obtained, for example 4-fluoro-3- bromo-benzotrifluoride and 4-methyl-3-bromo-benzotrifluoride, can be prepared using it.

Compounds of the formula

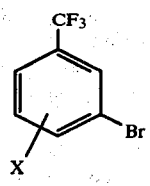

wherein
X denotes hydrogen, halogen or a $C_1$–$C_4$ alkyl radical, are formed by the process according to the invention.

The m-bromo-benzotrifluorides, especially the new compounds 4-fluoro-3-bromo-benzotrifluoride and 4-methyl-3-bromo-benzotrifluoride prepared by the inventive process, can be reacted with copper cyanide to give the corresponding 3-trifluoromethyl-benzonitriles (literature: U.S. Pat. No. 2,195,076), which are useful as agents for combating parasites (in analogy to DT-OS (German Published Specification) No. 2,344,601 and 2,344,603). Moreover, the 3-trifluoromethyl-benzonitriles are important intermediate products for plant protection agents and pharmaceuticals.

EXAMPLE 1

920 g of 4-chlorobenzotrichloride are initially introduced into an autoclave, 4 g of iron sulphide are added and 690 g of bromine are added dropwise at 50° C. in the course of 4 hours. The mixture is then subsequently stirred for 4 hours at 60° C., excess bromine is expelled with nitrogen and the mixture is cooled to −10° C. 1 kg of anhydrous hydrofluoric acid is added to the reaction mixture obtained, the autoclave is closed and the pressure is increased to 2 bars of nitrogen. The mixture is then warmed to 60° C. and the hydrogen chloride formed is let down via a reflux condenser with a regulating valve at about 7 bars. After 30 minutes, the mixture is heated to 80° to 85° C. for 6 hours and, after the evolution of gas has ended, is cooled and excess hydrofluoric acid is distilled off. The residue is fractionated in vacuo. This gives a fore-run of 60 g (boiling point$_{15}$:30° to 75° C.), which consists predominantly of 4-chlorobenzotrifluoride, and then a main run (boiling point$_{15}$:78° to 81° C.) of 790 g of 4-chloro-3-bromo-benzotrifluoride, which corresponds to a yield of 75% of theory, relative to the 4-chloro-benzotrifluoride employed.

EXAMPLE 2

920 g of 4-chlorobenzotrichloride and 3 g of iron powder are initially introduced, at 30° C., into a reaction vessel, 690 g of bromine are added dropwise in the course of 1 hour and the mixture is subsequently stirred for 6 hours at 30° C. The crude bromination product is freed from excess bromine at 40° C. and under a pressure of 1 mm in a thin film evaporator. The crude product is added, at 10° C., to 800 ml of anhydrous hydrofluoric acid, the autoclave is closed and fluorination is carried out under an initial pressure of nitrogen of 3 bars as in Example 1.

Fractional distillation gives 840 g of 4-chloro-3-bromo-benzotrifluoride as the main fraction at boiling point$_{15}$: 77° to 81° C., which corresponds to a yield of 81% of theory.

EXAMPLE 3

690 g of bromine are added dropwise, at 30° C., to 920 g of 2-chlorobenzotrichloride and 3 g of iron sulphide in the course of 1 hour. The mixture is then subsequently stirred for 6 hours at 30°C., excess bromine is separated off in a thin film evaporator and the reaction product is added to 800 g of anhydrous hydrofluoric acid in an autoclave. The pressure is increased to 3 bars of nitrogen and the mixture is heated to 70° C., the hydrochloric acid formed being removed at 10 bars. After 2 hours the reaction mixture is heated to 100° C. and kept at this temperature until the evolution of gas has ceased. After cooling, excess hydrofluoric acid is distilled off. After steam distillation, 2.5 l of a distillate are obtained, the organic phase of which is separated off; the organic phase is dried with sodium bisulphate.

The 900 g of crude product consist of: 1.7% of 2,5-dichlorobenzotrifluoride, 92.3% of 2-chloro-5-bromo-benzotrifluoride, 4.4% of 2-chloro-3-bromo-benzotrifluoride and 3% of a dibromo compound. The yield of chloro-bromo-benzotrifluorides is accordingly 84% of theory.

Pure 2-chloro-5-bromo-benzotrifluoride is obtained by distillation, boiling point: 198° to 199° C.; $n_D^{20}$: 1.5040.

EXAMPLE 4

585 g of benzotrichloride are initially introduced into the reaction vessel at 50° C. with 2 g of iron powder, 480 g of bromine are added dropwise in the course of 1 hour, the mixture is stirred for 4 hours at 50° C., the bromine is expelled by passing nitrogen through and the catalyst is then filtered off.

600 ml of anhydrous hydrofluoric acid are initially introduced into an apparatus for the fluorination reaction, the crude bromination product is added dropwise at −4° C. and the temperature is raised to 20° C. until the hydrogen chloride evolution has ended. The pressure is then increased with nitrogen, the mixture is warmed to 70° C. for 3 hours and cooled and excess hydrofluoric acid is distilled off. The organic residue is washed with 100 ml of 40% strength sodium bisulphide solution and then with 100 ml of water and the organic phase, which has been separated off, is dried with calcium chloride and subjected to fractional distillation. After a fore-run of 50 g of benzotrifluoride, 411 g (61% of theory) of 3-bromo-benzotrifluoride are obtained with a boiling point: 154° to 155° C.

EXAMPLE 5

120 g of bromine are added dropwise, at 50° to 55° C., to 157 g of 4-fluorobenzotrichloride and 1 g of iron sulphide in the course of 1 hour, the mixture is then subsequently stirred at 55° C. for 5 hours, and finally excess bromine is expelled with nitrogen.

The reaction mixture is then added dropwise to 160 ml of anhydrous hydrofluoric acid at 0° C. in a fluorinating apparatus, the mixture is warmed to 20° C., whilst stirring, the pressure is increased with nitrogen, the mixture is warmed to 70° C. for 7 hours and the hydrogen chloride evolved is separated off at 7.5 bars. After cooling to room temperature, excess hydrofluoric acid is distilled off and the residue is subjected to fractional distillation under 35 mm. After a fore-run of 10 g (boiling point$_{35}$: 32° to 40° C.), 94 g (52% of theory) of 4-fluoro-3-bromo-benzotrifluoride pass over at boiling point$_{35}$: 53° to 60° C.

EXAMPLE 6

0.5 g of iron sulphide is added to 240 g of 4-methyl-benzotrichloride and 160 g of bromine are added dropwise at 30° C. The mixture is stirred for 6 hours at 30° C. and excess bromine is then separated off by passing nitrogen through.

200 g of anhydrous hydrofluoric acid are initially introduced, at −10° C., into a fluorinating apparatus and the crude bromination product is then added dropwise. Thereafter, the hydrogen chloride evolution is allowed to subside in the course of about 3 hours at 18° C., the pressure is increased to 5 bars of nitrogen and the mixture is warmed to 70° C., the hydrogen chloride being separated off at about 8.5 bars. After about 2 hours, the mixture is cooled, excess hydrofluoric acid is distilled off and the crude product is subjected to fractional distillation. After a fore-run of 4-methylbenzotrifluoride, 146 g (corresponding to 61% of theory) of 3-bromo-4-methyl-benzotrifluoride are obtained at boiling point$_{14}$: 62° to 68° C.

What is claimed is:

1. A process for preparing m-bromo-benzotrifluorides which comprises contacting a benzotrichloride of the formula

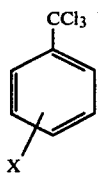

(I)

wherein
   X represents hydrogen, halogen or lower alkyl, with a source of bromine in the presence of a catalyst and thereafter fluorinating the resultant bromination product at an elevated temperature under an elevated pressure.

2. A process according to claim 1 wherein the fluorination is carried out at a temperature in the range of −10° to 120° C. under a pressure of 3 to 40 bars.

3. A process according to claim 2, wherein the fluorination is carried out at a temperature of 60° to 100° C. at a pressure of 6 to 10 bars.

4. A process according to claim 1 wherein the fluorination is effected employing hydrofluoric acid, or antimony trifluoride.

5. A process according to claim 1 wherein bromination is effected at a temperature of 0° to 100° C.

6. A process according to claim 5 where bromination is effected at a temperature of 20° to 70° C.

7. A process according to claim 6 wherein bromination is effected at a temperature of 30° to 60° C.

8. A process according to claim 5 wherein the catalyst is present in the amount of 0.2 to 1% by weight based upon the weight of the benzotrichloride.

9. A process according to claim 8 wherein the catalyst is present in the amount of 0.3 to 0.5% by weight based upon the amount of the benzotrichloride.

10. A process according to claim 5 wherein the catalyst present during the bromination is a Friedel Crafts catalyst.

11. 4-fluoro-3-bromo-benzotrifluoride.

12. 4-methyl-3-bromo-benzotrifluoride.

13. A process according to claim 1 wherein the fluorination of the brominated product is effected without separation of the brominated product from this reaction mixture.

* * * * *